US00PP36190P2

(12) United States Plant Patent
Smith et al.

(10) Patent No.: US PP36,190 P2
(45) Date of Patent: Oct. 8, 2024

(54) ***ARABIS* PLANT NAMED 'Arctic Fox'**

(50) Latin Name: ***Arabis* x *sturrii***
Varietal Denomination: Arctic Fox

(71) Applicants: Michael Vern Smith, Scappoose, OR (US); Maurice Horn, Scappoose, OR (US)

(72) Inventors: Michael Vern Smith, Scappoose, OR (US); Maurice Horn, Scappoose, OR (US)

( * ) Notice: Subject to any disclaimer, the term of this patent is extended or adjusted under 35 U.S.C. 154(b) by 0 days.

(21) Appl. No.: 18/437,021

(22) Filed: Feb. 8, 2024

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 6/20; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new variety of Arabis (species x *sturrii*) named 'Arctic Fox' which exhibits an exceptionally low-growing and spreading plant habit and striking green and white variegated semi-glossy foliage consisting of mid-green leaf centers surrounded by light cream leaf margins and marginal bands. 'Arctic Fox' bears pure white colored flowers in dense racemes on stems which rise 5 cm to 10 cm above the ground or base level of the mat of foliage. The petals of the flowers of 'Arctic Fox' are free, unlobed, white in color, ovate and glabrous. The anthers of the flowers of 'Arctic Fox' (six in number) and are grey-green in color and conspicuous against the white-colored petals.

2 Drawing Sheets

Genus and species: *Arabis* x *sturrii.*
Variety denomination: 'Arctic Fox'.

BACKGROUND

The present invention relates to a new and distinct cultivar of Rock Cress plant grown as a showy ornamental plant for planting in rock gardens or troughs and as a groundcover for the landscape. The new variety is known botanically as *Arabis* x *sturrii* and will be referred to hereinafter by the cultivar name 'Arctic Fox'.

'Arctic Fox' was discovered by the inventors as a naturally occurring branch sport found growing on an unnamed plant of the species *Arabis* x *sturrii* (unpatented). *Arabis* x *sturrii* which is included in the family of Brassicaceae is a stoloniferous plant which bears densely ground hugging vegetative rosettes of entirely green foliage. The inventors discovered first observed 'Arctic Fox' in 1999 amongst plants of *Arabis* x *sturrii* which the inventors had raised and were growing at their specialty plant nursery in Scappoose, Oregon. 'Arctic Fox' exhibits striking green and white carpet-forming variegated foliage. As is typical of the species *Arabis* x *sturrii*, 'Arctic Fox' produces paniculate racemes of tiny sterile white flowers in and from early spring.

The inventors were attracted to the striking green and white variegated foliage whose overall effect in containers and in the landscape is of a dense mat of contrasting foliage covered in spring and early summer with many densely packed racemes consisting of pure white flowers.

'Arctic Fox' can be compared with its sport parent and the species *Arabis* x *sturrii*. Whereas the foliage of *Arabis* x *sturrii* is entirely green in color, the foliage of 'Arctic Fox' is strikingly variegated consisting of mid-green leaf centers surrounded by white to light cream marginal bands.

'Arctic Fox' was first asexually propagated by the inventors at their nursery in Scappoose, Oregon using the method of basal rosette stem cuttings. The inventors have carried out multiple asexual reproductions and have confirmed that the variegation of 'Arctic Fox' is uniform and stable and reproduces true to type from its cuttings.

SUMMARY

The following traits have been repeatedly observed and represent the distinguishing characteristics of the new *Arabis* variety known as 'Arctic Fox.' These traits in combination distinguish 'Arctic Fox' from all other existing varieties of *Arabis* known to the inventor. 'Arctic Fox' has not been tested under all possible conditions and phenotypic differences may be observed with variations in environmental, climatic, and cultural conditions, however, without any variance in genotype. Growing requirements are similar to the species.

1. 'Arctic Fox' exhibits an exceptionally low-growing and spreading plant habit.
2. 'Arctic Fox' exhibits striking green and white variegated semi-glossy foliage consisting of mid-green leaf centers surrounded by light cream leaf margins and marginal zones.
3. 'Arctic Fox' exhibits pure white colored flowers borne conspicuously in dense racemes on stems which rise 5 cm to 10 cm above the ground level mat of foliage.
4. The petals of the flowers of 'Arctic Fox' are free, unlobed, white in color, ovate and glabrous.

5. The anthers of the flowers of 'Arctic Fox' (six in number) are grey-green in color and conspicuous against the white-colored petals.
6. During one season of growth from over-wintering, 'Arctic Fox' reaches 15 cm in diameter 4 cm in maximum height where the foliage is crowded and elevated.
7. 'Arctic Fox' blooms profusely from late spring through summer.
8. 'Arctic Fox' is hardy to USDA Zone 4.

BRIEF DESCRIPTION OF THE DRAWINGS

The accompanying color drawings illustrate the overall appearance of the new *Arabis* variety named 'Arctic Fox' showing colors as true as it is reasonably possible to obtain in colored reproductions of this type.

The drawing labeled

Figure 1:
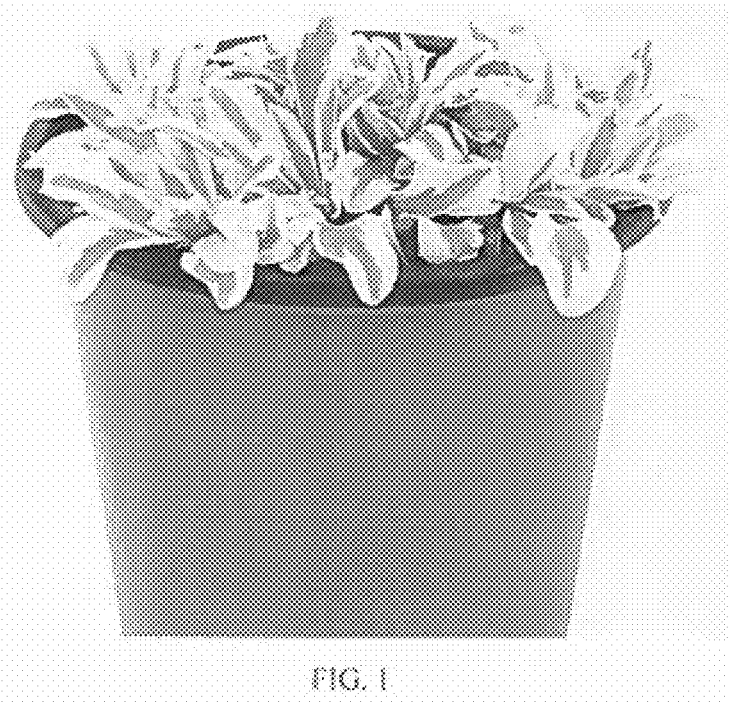
FIG. 1 depicts a close-up view of the variegated foliage of 'Arctic Fox' growing on a one year old plant which has been established in a 1-gallon container in Santa Barbara, California. The illustrated plant has been grown in sun under very light shade The drawing labeled
Figure 2:
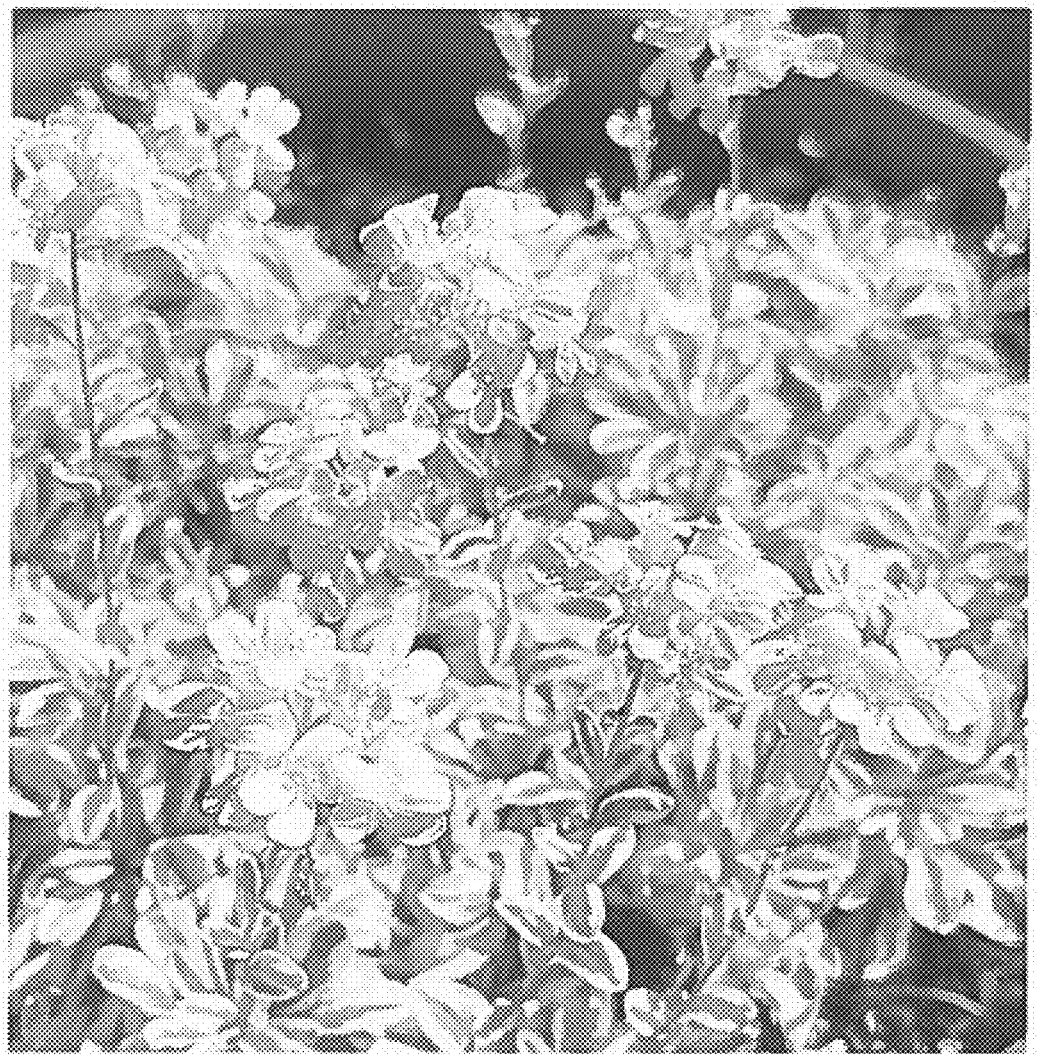
FIG. 2 is a close up of the inflorescence of 'Arctic Fox'. This drawing was made from a photograph taken in mid-July when flowering is almost finished.

Colors in the drawings may differ from color values cited in the detailed botanical description, which accurately describe the actual color of the new *Arabis* variety named 'Arctic Fox'. All drawings were made using conventional techniques and although foliage colors may appear different from actual colors due to light reflectance, they are as accurate as possible by conventional photography.

BOTANICAL DESCRIPTION OF THE PLANT

The following is a detailed description of the new *Arabis* cultivar named 'Arctic Fox'. Data was collected in Santa Barbara, California in August 2023 from an established 15-month-old plant which was growing out of doors in very light shade in a 2-gallon container. Phenotypic differences may be observed with variations in environmental, climatic, and cultural conditions, without however, any difference in genotype. Color determinations are in accordance with the fifth edition (2007) of The Royal Horticultural Society Colour Chart except where general color terms of ordinary dictionary significance are used. The growing requirements are similar to the species.

Classification:

*Botanical classification.*—*Arabis* x *sturrii.*
*Family.*—Brassicaceae.
*Genus.*—*Arabis.*
*Species.*—x *sturrii.*
*Denomination.*—'Arctic Fox'.
*Common name.*—Rock Cress.

Plant:

*Plant type.*—Herbaceous alpine perennial ground cover.
*Plant use.*—Border, rock garden, in containers and as a groundcover for the landscape.
*Plant parentage.*—'Arctic Fox' is a naturally occurring branch sport of an unnamed plant of *Arabis* x *sturrii* (species, unpatented).
*Plant vigor.*—Slow spreading growth and very slow upright growth.
*Branching habit.*—Profuse basal branching as the cauline leaves clasp the basal nodes of each newly produced stoloniferous rosette.
*Dimensions at maturity.*—15 cm in diameter and up to 4 cm in maximum height.
*Plant hardiness.*—USDA Zone 4.
*Asexual propagation method.*—Excision and rooting of softwood cuttings and cauline rosettes. Well-established plants may be increased by multiple divisions of the entire mass of foliage.
*Growth habit.*—Low and spreading. Stems may root where a node is in contact with soil surface. Variety makes a good ground cover.
*Root system.*—Fine and fibrous. Root color 163D.
*Cultural requirements.*—Plant in well-draining soil, in good light but avoiding direct unfiltered sun. Ensure that rooting zone remains moist but not excessively wet. The incorporation of sharp grit in the planting mix will encourage root growth and minimize waterlogging.
*Planting conditions.*—'Arctic Fox' is both drought-tolerant and humidity tolerant.
*Time to initiate roots.*—2 weeks to develop roots on an initial cutting.
*Crop time.*—8-10 weeks from a rooted cutting to a finished commercial 1-litre container whose surface is at least 75% covered by the foliage.
*Seasonal interest.*—Flowers from late spring and early summer.

Stems:

*General.*—Plants are acaulescent; stems are observed as above-ground stolons bearing basal leaves and terminating with leaflet rosettes.
*Stem shape.*—Cylindrical; stem terminates at base of first leaf pair and is barren below.
*Stem surface.*—Puberulent.
*Stem length.*—Very short, ranging between 5 mm and 20 mm.
*Stem diameter.*—1.5 mm-2.0 mm.
*Stem color.*—194D.
*Internodal distance.*—0 cm.

Foliage (Basal Leaves, i.e. leaves borne on basal stems below rosette of terminal leaflets):

*Basal leaf arrangement.*—Opposite.
*Basal leaf division.*—Simple.
*Basal leaf shape.*—Elliptic.
*Basal leaf apex.*—Acute.
*Basal leaf base.*—Cuneate.
*Basal leaf attachment.*—Sessile.

Foliage (Terminal Leaves present in whorled rosettes at terminals of basal stems):

*Rosette diameter.*—Up to 4 cm.
*Terminal leaves per rosette.*—5-6 leaves in each whorl, 20-25 leaves altogether.
*Terminal rosette leaf dimensions.*—Up to 4 cm in length and 7 mm in width.
*Terminal rosette leaf shape.*—Narrowly elliptic.
*Terminal rosette leaf apex.*—Acute.
*Terminal rosette leaf base.*—Truncate.
*Terminal rosette leaf attachment.*—Sessile.
*Terminal rosette leaf margin.*—Minutely crenulate.
*Terminal rosette leaf surface* (*adaxial surface*).—Glabrous and glossy.
*Terminal rosette leaf surface* (*abaxial surface*).—Matte, lightly scabrous.

*Terminal leaf color* (*adaxial surface, mid-green center*).—136B.

*Terminal leaf color* (*adaxial surface, light cream margins*).—NN155D.

*Extent of variegated region*.—Light cream margin extends entirely and mostly symmetrically around the leaf margin and 3 mm-4 mm inward from margin towards mid-green center.

*Venation Pattern*.—Pinnate, veins only visible as white or light cream veins within both surfaces of the green leaf centers.

*Vein color* (*both surfaces*).—157D.

*Foliar fragrance*.—None observed.

Inflorescence:

*Inflorescence type*.—Terminal raceme.

*Inflorescence dimensions*.—Overall, 12 cm in length to first flower emergence. 22 cm in length when fully flowering and flowers approach senescence. Diameter of inflorescence between 4 cm and 7 cm.

*Inflorescence quantity*.—Ranges from 5 (early spring) to 25 (mid-summer) per 1-gallon container plant.

*Blooming season*.—mid-April to late June.

*Flower quantity*.—Between 5 and 20 per inflorescence.

*Flower shape*.—Radially symmetrical.

*Flower dimensions*.—16 mm in height and 8 mm in width.

*Distance between flowers* (*peduncle spacing*).—4-5 mm.

*Corolla tube depth*.—1 mm.

*Number of petals*.—4 in number.

*Petal color* (*adaxial and abaxial surfaces*).—Ranges between 94A and 94B.

*Corolla tube color*.—NN155D.

*Petal length*.—Ranges from 6 mm to 8 mm.

*Petal width*.—Ranges from 3 mm to 4 mm.

*Petal shape*.—Broadly obovate, unlobed.

*Petal apex*.—Rounded.

*Petal base*.—Truncate.

*Petal Margin*.—Entire.

*Petal surface* (*adaxial and abaxial surfaces*).—Glabrous.

*Peduncle length*.—Average is 4 mm.

*Peduncle diameter*.—0.5 mm.

*Peduncle color*.—138B.

*Peduncle shape*.—Cylindrical.

*Peduncle surface*.—Smooth.

*Calyx shape*.—Funnelform.

*Calyx diameter* (*when flattened*).—8 mm.

*Calyx color*.—138B.

*Sepals*.—4 in number arranged as two pairs: one pair of adjacent long sepals opposite to one pair of adjacent short sepals).

*Sepals fused or unfused*.—Unfused.

*Sepal dimensions*.—Longer pair 7 mm×2 mm, shorter pair 3-4 mm×1 mm.

*Sepal shape*.—Lanceolate.

*Sepal margin*.—Entire.

*Sepal color* (*adaxial and abaxial surfaces*).—138B.

*Sepal apex*.—Acute.

*Sepal surface*.—Smooth.

*Bud dimensions*.—8 mm in length and 4 mm in diameter.

*Bud color*.—155B.

*Bud shape*.—Ovoid, apex and base rounded.

*Bud surface*.—Smooth.

*Flower fragrance*.—None observed.

Reproductive organs:

*Stamens*.—6 in number, terete.

*Stamen length*.—From 3 mm to 5 mm.

*Stamen diameter*.—1 mm to 1.5 mm.

*Stamen color*.—Dark cream, between 155A and 160D.

*Anther shape*.—Club, bifid.

*Anther dimensions*.—1 mm in length and less than 0.50 mm in width.

*Anther color*.—153A.

*Pollen*.—Moderate amount, color NN155B.

*Pistil*.—1 in number.

*Pistil length*.—4 mm.

*Pistil color*.—160D.

*Stigma shape*.—Bi-lobed, rounded.

*Stigma surface*.—Glossy.

*Stigma color*.—85D.

*Stigma height*.—Less than 0.50 mm.

*Ovary shape*.—Globose.

*Ovary dimensions*.—Less than 1 mm in diameter and less than 1 mm in height.

*Ovary color*.—145D.

*Ovary position*.—Superior.

Fruit: Pods, sparse, linear, cylindrical, containing two parallel rows of seeds.

*Seeds*.—Very few present and observed immature (soft) only.

*Shape*.—Ovoid up to 3 mm in length.

*Seed color*.—N144A.

We claim:

1. A new and distinct variety of *Arabis* plant named 'Arctic Fox' as described and illustrated herein.

* * * * *